US005230351A

United States Patent [19]

Nyorkor

[11] Patent Number: 5,230,351

[45] Date of Patent: Jul. 27, 1993

[54] COMBINATION HAND AND FINGER CUFF

[76] Inventor: Sahr A. A. Nyorkor, 6550 E. 55th Pl., Indianapolis, Ind. 46226

[21] Appl. No.: 930,270

[22] Filed: Aug. 14, 1992

[51] Int. Cl.[5] A61F 5/37; E05B 75/00

[52] U.S. Cl. 128/878; 70/16

[58] Field of Search 128/878, 879; 602/20, 602/21; 70/16, 17; 2/16, 66, 162, 159, 160

[56] References Cited

U.S. PATENT DOCUMENTS

| | | | |
|---|---|---|---|
| 404,544 | 6/1889 | James | 70/16 |
| 2,516,241 | 7/1950 | Mulheran | 2/160 |
| 3,253,589 | 5/1966 | Shook | 2/16 |
| 4,024,863 | 5/1977 | Ball | 70/16 |
| 4,469,096 | 9/1984 | Rivadeneyra | 128/879 |
| 4,741,051 | 5/1988 | Bible | 70/16 |
| 4,949,679 | 8/1990 | Wolfer | 128/878 |
| 4,977,625 | 12/1990 | Charters | 602/21 |
| 5,031,641 | 7/1991 | Upton | 70/16 |

*Primary Examiner*—Michael A. Brown

*Attorney, Agent, or Firm*—Richard L. Miller

[57] ABSTRACT

A combination hand and finger cuff is provided which consists of a handcuff, with a pair of rigid gloves fastened each at a wrist portion thereto. The hands of a person may inserted into the rigid gloves and the handcuffs locked about the wrists of the person, whereby the rigid gloves will restrain and confine the hands of the person. Accordingly a person so confined cannot hold any objects, thereby avoiding the danger of injury to themselves and others.

4 Claims, 1 Drawing Sheet

COMBINATION HAND AND FINGER CUFF

SUMMARY OF THE INVENTION

A primary object of the present invention is to provide a combination hand and finger cuff that will overcome the shortcomings of the prior art devices.

Another object is to provide combination hand and finger cuffs, that utilizes a pair of rigid gloves, with each connected at the wrist portion to a locking hoop of a respective handcuff to better restrain and confine the hands of a person.

An additional object is to provide a combination hand and finger cuff that will prevent the fingers of the person from moving, so that the person cannot hold any objects, which will avoid the danger of injury to themselves and others.

A further object is to provide a combination hand and finger cuff that is simple and easy to use.

A still further object is to provide a combination hand and finger cuff that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only and that changes may be made in the specific construction illustrated and described within the scope of the appended claims.

BRIEF DESCRIPTION OF THE DRAWING FIGURES

The figures in the drawings are briefly described as follows.

Figure 2:
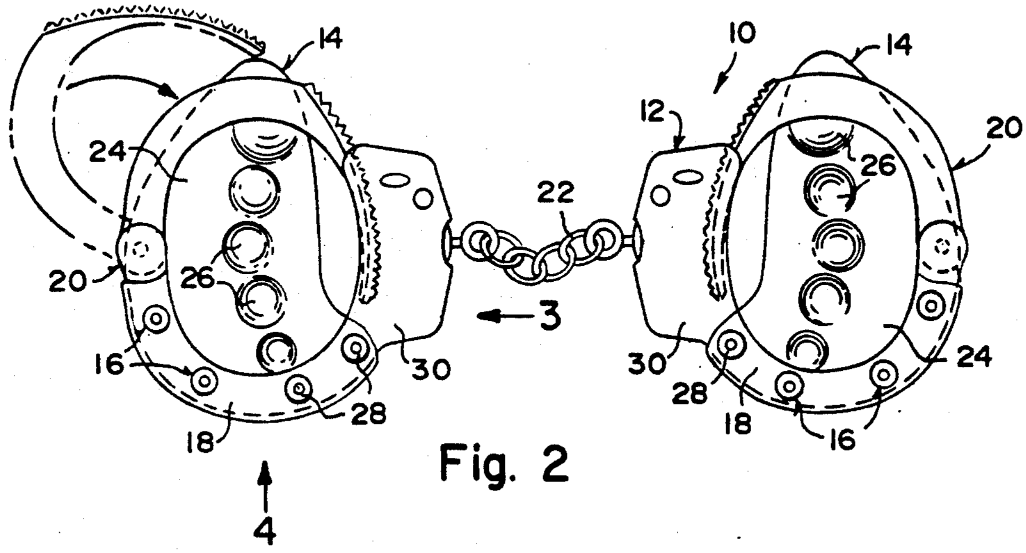
FIG. 2 is a diagrammatic elevational view taken in the direction of arrow 2 in FIGS. 1, 3 and 4.
Figure 3:
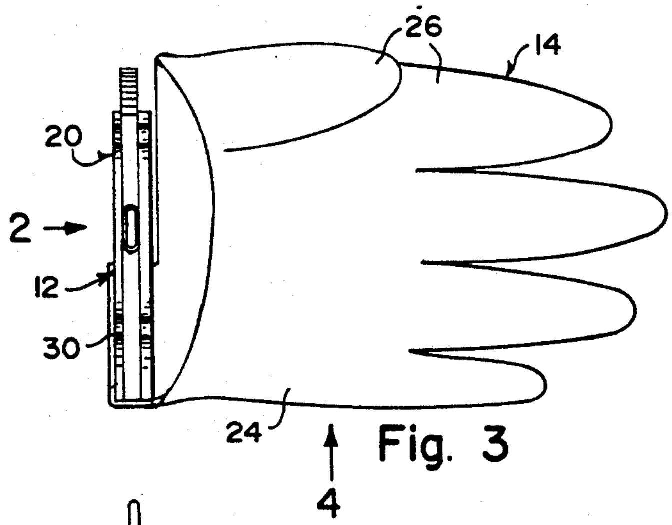
Figure 4:
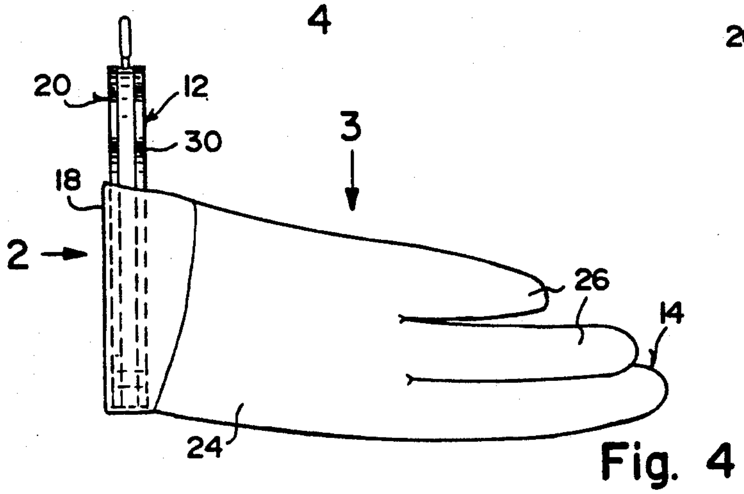
Figure 1:
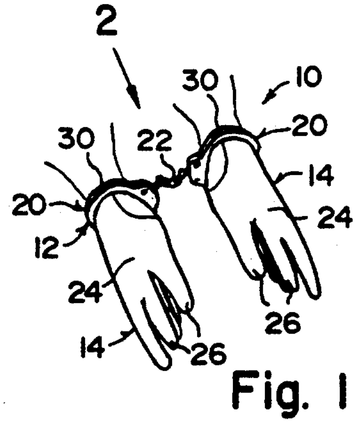
FIG. 1 is a perspective view of the instant invention in use.

FIG. 3 is a side elevational view with parts broken away taken in the direction of arrow 3 in FIGS. 2 and 4; and FIG. 4 is an elevational view with parts broken away taken in the direction of arrow 4 in FIGS. 2 and 3.

DETAILED DESCRIPTION OF THE PREFERRED EMBODIMENTS

Turning now descriptively to the drawings, in which similar reference characters denote similar elements throughout the several views, the Figures illustrate combination hand and finger cuffs 10 which consists of a pair of cuffs 12, a pair of rigid gloves 14 and fasteners 16 for securing a wrist portion 18 of each rigid glove 14 to the handcuff 12. After the hands of a person are inserted into the rigid gloves 14 and a respective handcuff 12 is locked about the wrists of the person, the rigid gloves 14 will restrain and confine the hands of the person. The person cannot hold any objects, thereby avoiding the danger of injury to themselves and others.

The pair of handcuffs 12 includes a pair of adjustable hoops 20 that can be tightened and locked about the wrists of the person. The adjustable hoops include a first and a second hoop arms that are pivotally linked together as if FIG. 2. A short attaching linkage 22 formed typically out of metal chain is connected between the hoops 20, which can be fabricated typically out of metal, so as to keep the wrists of the person close together and limit the movement of the hands of the person.

Each rigid glove 14 is fabricated out of an inflexible fitted covering 24, typically but not limited to metal or plastic, for the hand with a separate sheath 26 for each finger and thumb that is molded thereto, so as to prevent bending of the fingers and the thumb.

The securing fasteners 16 are typically a plurality of rivets 28, that will permanently secure the wrist portion 18 of each rigid glove 14 to a portion 30 of each respective adjustable metal hoop 20.

In operational use a person's hands are inserted into the rigid gloves 14 and than the handcuffs 12 are tightened about the wrists so as to restrain and confine the hands thereby preventing the person from handling objects typically guns, knifes or other weapons which accordingly precludes them from easily injuring others, or even their own person.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. Combination hand and finger cuffs which comprises:

a) a pair of handcuffs b) a pair of rigid gloves; and c) means for securing a wrist portion of each said rigid glove to a respective handcuff, so that after the hands of a person are inserted into said rigid gloves and the handcuffs are locked about the wrists of the person, said rigid gloves will restrain and confine the hands of the person, thereby preventing the person from holding any objects accordingly avoiding the danger of injury to themselves and others and each said rigid gloves being fabricated out of an inflexible fitted covering for the hand with a separate sheath for each finger and thumb, so as to prevent the bending of the fingers and the thumb.

2. Combination hand and finger cuffs as recited in claim 1, wherein said handcuff includes:

a) a pair of adjustable hoops that can be tightened and locked about the wrists of the person; and b) a short attaching linkage connected between said hoops, so as to keep the wrists of the person close together and limit the movement of the hands of the person.

3. Combination hand and finger cuffs as recited in claim 2, wherein said securing means includes a plurality of rivet fasteners permanently attached to each wrist portion and a portion of each adjustable hoop, that will permanently secure the wrist portion of each said rigid glove to the portion of each said respective adjustable hoop.

4. Combination hand and finger cuffs as recited in claim 3, wherein the adjustable hoops each comprise first and second hoop arms pivotally linked together at one of their respective ends for pivotal movement in a common plane relatively apart and together between open, hand and wrist admitting and closed hand and wrist confining positions thereof, the hoop portion through which the rivet fasteners are permanently attached is a part of only the first hoop arm and the glove extending forwardly therefrom with a remainder of a periphery of a rear end of the glove being cut away to extend clear of the plane of movement of the second hoop arm thereby permitting the relative pivotal movement of the arms.

* * * * *